United States Patent [19]

Harke

[11] Patent Number: 4,831,639
[45] Date of Patent: May 16, 1989

[54] COMPUTER TOMOGRAPHY APPARATUS

[75] Inventor: Wolf-Udo Harke, Sandhausen, Fed. Rep. of Germany

[73] Assignee: Siemens Aktiengesellschaft, Berlin and Munich, Fed. Rep. of Germany

[21] Appl. No.: 176,327

[22] Filed: Mar. 31, 1988

[30] Foreign Application Priority Data

May 15, 1987 [DE] Fed. Rep. of Germany ... 8707038[U]

[51] Int. Cl.⁴ .................... G01T 1/24; G03G 41/16
[52] U.S. Cl. ............................... 378/19; 378/4; 250/370.15
[58] Field of Search ............... 378/4, 15, 18, 19, 199, 378/200; 62/381, 514 R, 499; 250/370.15

[56] References Cited

U.S. PATENT DOCUMENTS

| 4,456,826 | 6/1984 | Forster | 378/19 |
| 4,571,495 | 2/1986 | Distler et al. | 378/4 |
| 4,651,338 | 3/1987 | Hahn | 378/199 |
| 4,709,559 | 12/1987 | Dotzauer et al. | 378/200 |

FOREIGN PATENT DOCUMENTS

| 109206 | 5/1984 | European Pat. Off. . |
| 8707038 | 5/1987 | European Pat. Off. . |
| 57-50673 | 7/1982 | Japan . |
| 0052587 | 3/1983 | Japan ............................ 250/370.15 |
| 2026812 | 2/1980 | United Kingdom . |

Primary Examiner—Janice A. Howell
Assistant Examiner—Joseph A. Hynds

[57] ABSTRACT

A computer tomography apparatus with a frame upon which is mounted an x-ray emitter and corresponding detector module with x-ray detectors and associated electronics, is provided with a closed circulation cooling system with evaporator coils located adjacent to the electronics, the coils lying across both focus-proximate and focus-distant edges of circuit boards for the electronics, a condensor located away from the electronics, and cooling air which is blown through interspaces between the circuit boards and the evaporator coils.

9 Claims, 3 Drawing Sheets

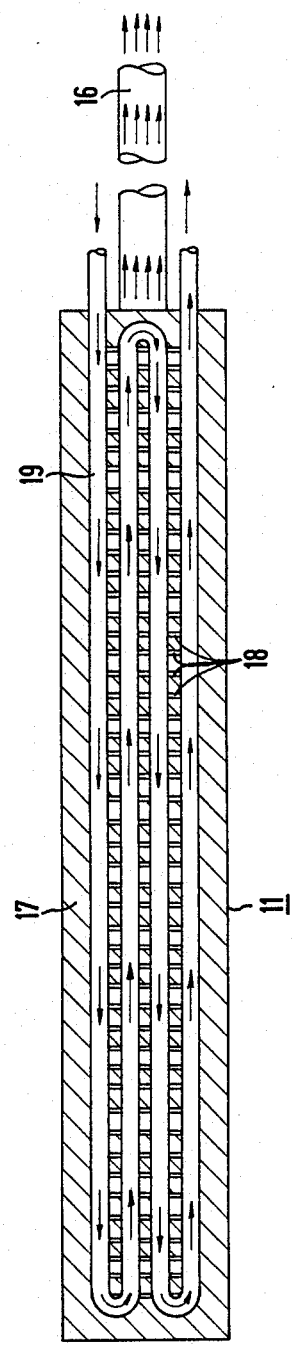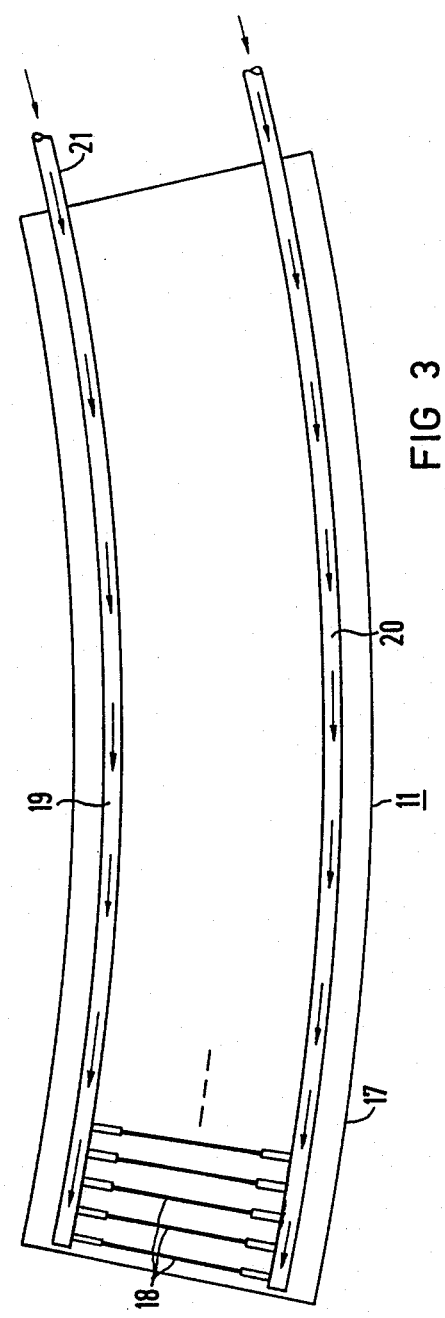

COMPUTER TOMOGRAPHY APPARATUS

BACKGROUND OF THE INVENTION

1. Field of the Invention

The invention is directed generally to a computer tomography apparatus with a rotating frame on which an x-ray emitter, a radiation detector, and associated detector electronic components are carried and, particularly, to a cooling system for the associated detector electronic components.

2. Discussion of the Related Art

In the art relating to computer tomography or zeugmatography, an x-ray emitter or radiator is located on an annular frame which rotates about a patient placed in a center hole of the frame. The x-ray emitter emits fan-shaped beam of x-rays through the patient which are picked up by detectors aligned with the focal point of the x-ray radiator. In this manner, cross-sectional or transversal slice images of the patient's body are produced.

It has long been noted that the electronic components associated with the detectors, the so-called electronics, generate a great amount of undesirable heat. As a result, attempts have been made to effectively remove or eliminate the heat generated by the electronics associated with the computer tomography apparatus detectors.

German patent application No. 34 36 867 discloses one attempted solution. A computer tomography apparatus is provided with a channel between the rotating frame and the stationary frame. The channel is traversed by a coolant. Additionally, cooling ribs of the rotating frame project into the channel.

Japanese patent application No. 57-50673 discloses a computer tomography apparatus wherein individual detectors are located in a collimator, mainly upon collimator plates. The collimator plates serve as cooling fins for the detectors. Additionally, cooling lines containing coolant are provided which penetrate through the fins to carry heat away from the fins. However, no disclosure is made as to the type of coolant used. Furthermore, no disclosure is made as to whether the electronics associated with the detectors are similarly cooled.

European patent application No. 0 109 206 discloses a fourth generation computer tomography apparatus which includes a stationary detector ring with detector modules. The detector ring is cooled by cooling air that is blown into the detector modules through channels or shrouds. The cooling air circulates within a closed circulation system which includes evaporators located on the stationary ring. The cooling coils of the evaporators are not employed directly at the electronics associated with the detectors.

British patent application No. 2 026 812 discloses a third generation computer tomography apparatus which employs a closed circulation cooling system having coolant pumps and an x-radiator mounted on a rotating frame. Oil is used as the coolant. Neither an evaporator nor a condensor are utilized. Moreover, the cooling oil is used primarily to cool the x-ray tube and not the detector electronics.

SUMMARY OF THE INVENTION

An object of the invention is to provide a computer tomography apparatus in which an effective cooling of the detector electronics is assured. This object is achieved in accordance with the invention by providing a computer tomography apparatus with a rotating frame which carries a closed cooling circulation system, wherein an evaporator in the form of cooling coils is placed adjacent to the electronics and a condensor is placed at a distance from the electronics. An intense cooling of the electronics is assured because the evaporator is located adjacent to the electronics and the heat generated by the electronics is removed effectively by the coolant as it expands within the evaporator coils In a preferred embodiment of the invention, wherein the electronics associated with the detectors are located on a series or row of printed circuit boards that are aligned roughly with the focus of the x-ray emitter, the series or row of circuit boards is covered by cooling coils at both focus-proximate and focus-distant sides and cooling air is blown between interspaces between the circuit boards and the cooling coils.

The selection of materials for the housing parts of the electronics is made with a view toward optimizing heat elimination. Therefore, an aluminum panel for supporting the evaporator coils is utilized that has black surfaces to reduce thermal resistance between them. The housing has polished inner surfaces to reflect heat to force removal of the heat through the closed circulation cooling system.

These and other objects and aspects will be apparent with reference to the description of the preferred embodiment and the attached drawings.

BRIEF DESCRIPTION OF THE DRAWINGS

FIG. 2 is a cross-sectional top view of the detector module of the tomography apparatus of FIG. 1 showing the arrangement of the cooling coils with respect to the circuit boards of the electronics;

FIG. 3 is a cross-sectional side view of the detector module of the tomography apparatus of FIG. 1 showing the arrangement of the cooling coils with respect to the circuit boards of the electronics.

DESCRIPTION OF THE PREFERRED EMBODIMENT

Figure 1:
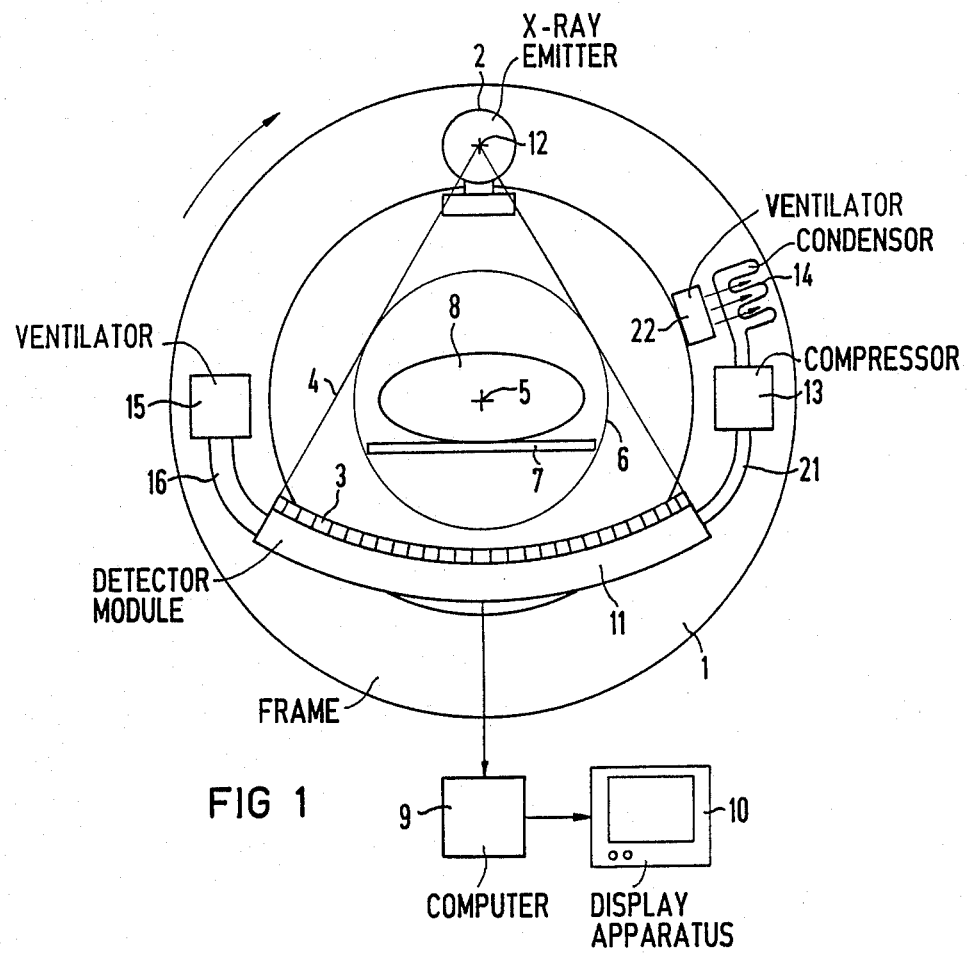
FIG. 1 is a schematic diagram of a computer tomography apparatus embodying principles of the invention.

In FIG. 1 there is shown a computer tomography apparatus in schematic form embodying principles of the invention. The computer tomography apparatus includes a rotating frame 1 having an x-ray emitter or radiator 2 and x-ray detectors 3 mounted thereon. The x-ray emitter has a focus or focal point 12. The x-ray detectors 3 are composed of a row or series of individual detectors, for example, 512 detectors. The x-ray emitter 2 has a diaphragm or iris for gating a fan-shaped x-ray beam 4, margin rays of which are tangential to a measuring field 6 given rotation of the rotating frame 1 about an axis 5. A patient support 7, upon which a patient 8 who is to be examined lies, is located within the measuring field 6.

In operation, the patient 8 is transirradiated from various directions by rotating the frame 1. The individual x-ray detectors 3 detect x-rays passing through the body of the patient 8 and generate electrical signals from which a computer 9 calculates an image of a transversal slice of the patient 8. The image is reproduced on a viewing device 10.

The x-ray detectors 3 have electronic components, so-called electronics, associated with them which are arranged in a detector module 11. The electronics serve to integrate and process the output signals of the x-ray detectors 3 and are mounted on printed circuit boards 18 (shown in FIGS. 2-4).

Figure 4:
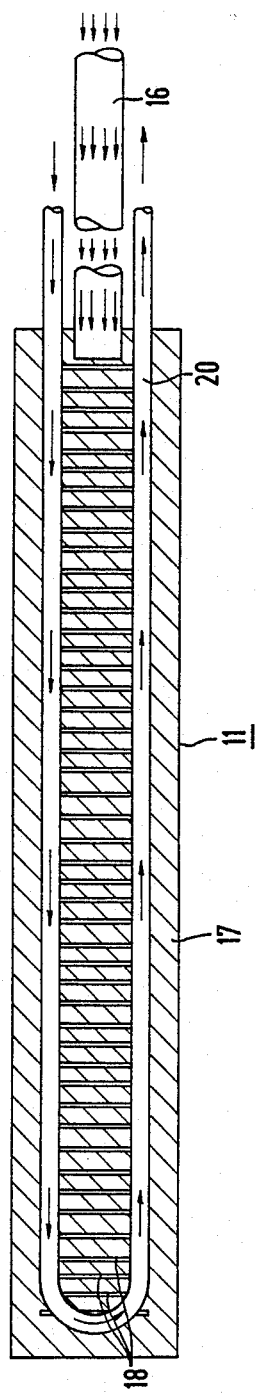
FIG. 4 is a cross-sectional bottom view of the detector module of the tomography apparatus of FIG. 1 showing the arrangement of the cooling coils with respect to the circuit boards of the electronics.

A closed circulation cooling system is included which has a compressor 13, a condensor 14, and evaporator coils 19 and 20 (shown in FIGS. 2-4). The cooling system serves to cool the electronics mounted on the circuit boards 18. A ventilator 15 blows air via a supply/return double conduit 16 through interspaces between the circuit boards 18 and the coils 19 and 20 to ensure rapid elimination of heat from the electronics. Another ventilator 22 is included on the frame 1 to cool the condensor 14.

In FIG. 2, there is shown a housing 17 for the electronics, preferably the detector module 11 itself, including the printed circuit boards 18 and the evaporator coil 19 in a cross-sectional view taken looking into the detector module 11 in the direction of the x-ray detectors 3. As is shown, the evaporator coil 19 includes multiple coils and winds over all of the circuit boards 18 on their focus-proximate ends (i.e., on the ends of the boards 18 nearest the x-ray emitter 2). Additionally, it is shown that the cooling air is blown into the electronics housing 17 through the conduit 16. The cooling air is also removed from the electronics housing 17 via the conduit 16 as it is constructed as a double conduit.

In FIG. 3 there is shown a cross-sectional side view of the detector module 11 in which it can be seen the evaporator coil 20 is located on the focus-distant edge of the circuit boards 18. Together, the coils 19 and 20 form the evaporator of the closed circulation cooling system. The coils are connected to the compressor 13 via conduit 21.

In FIG. 4, there is shown another cross-sectional view of the electronics housing 17, this time looking toward the detectors from the underside of the detector module 11. Again the cooling air supply/return conduit 16 can be seen. Additionally, the evaporator coil 20 is shown covering all of the circuit boards 18 with a single coil.

The sides of the housing 17 are preferably made of polished sheet steel to reflect the heat generated by the electronics while the coils 19 and 20 are preferably mounted o an aluminum panel to ensure better thermal conductivity. The aluminum panel is preferably anodized black to achieve a low thermal resistance. The floor and cover of the housing are preferably also made of polished sheet steel to guarantee a higher thermal resistance so that heat is not radiated towards the outside, but instead is removed only via the closed circulation cooling system.

Finally, the housing 17 is made radio frequency wave tight, i.e., the electronics are shielded from the x-rays emitted by the x-ray emitter 2.

While a preferred embodiment has been described, modifications or alterations may be apparent to those skilled in the art which still render a structure with the spirit and scope of the invention. For example, the invention could just as easily be employed on a computer tomography apparatus with a stationary frame. It is intended that the attached claims cover such modifications and alterations as well.

I claim:

1. A computer tomography apparatus for examining a subject, said apparatus comprising:
   a rotating frame surrounding said subject;
   mean mounted on said frame for irradiating said subject with x-rays;
   detector means mounted on said frame for detecting x-rays attenuated by said subject;
   electronic means connected to said detector means for processing signals generated by said detector means, said electronic means generating heat during said processing; and
   a closed circulation cooling system mounted on said frame for dissipating the heat generated by said electronic means,
   said cooling system including evaporator coils located at and in contact with said electronic means and a condensor located remote from said electronic means.

2. A computer tomography apparatus as set forth in claim 1, wherein said means for irradiating has a focus and wherein said electronic means comprises a row of printed circuit boards that are substantially aligned with said focus such that each printed circuit boards has a focus-proximate edge and a opposite focus-distant edge.

3. A computer tomography apparatus as set forth in claim 2, wherein said evaporator comprises a plurality of coils located above and below said printed circuit boards, at least one coil being located on said focus-proximate edges of said circuit boards, and one coil located across said focus-distant edges of said circuit boards.

4. A computer tomography apparatus as set forth in claim 3, further comprising means for blowing air between said circuit boards and said coils.

5. A computer tomography apparatus as set forth in claim 4, further comprising a housing for said electronics having heat reflective sides.

6. A computer tomography apparatus as set forth in claim 5, wherein said housing sides consist of polished sheet steel.

7. A computer tomography apparatus as set forth in claim 5, wherein said housing further comprises a panel supporting said coils which has a low thermal resistance.

8. A computer tomography apparatus as set forth in claim 7, wherein said panel consists of aluminum.

9. A computer tomography apparatus as set forth in claim 8, wherein said panel is anodized black.

* * * * *